United States Patent [19]

Beech, Jr. et al.

[11] Patent Number: 5,162,591
[45] Date of Patent: Nov. 10, 1992

[54] CATALYTIC OLEFIN HYDRATION FOR ETHER PRODUCTION

[75] Inventors: James H. Beech, Jr., Wilmington, Del.; James A. Stoos, Blackwood; Francis P. Ragonese, Cherry Hill, both of N.J.

[73] Assignee: Mobil Oil Corporation, Fairfax, Va.

[21] Appl. No.: 557,241

[22] Filed: Jul. 25, 1990

[51] Int. Cl.$^5$ .................. C07C 41/06; C07C 41/01
[52] U.S. Cl. .................. 568/695; 568/697; 568/897
[58] Field of Search .............. 568/695, 897, 697

[56] References Cited

U.S. PATENT DOCUMENTS

| | | | |
|---|---|---|---|
| 4,269,781 | 5/1981 | Vanderspurt et al. | 260/410.9 R |
| 4,334,890 | 6/1982 | Kochar et al. | 568/895 |
| 4,414,397 | 11/1983 | Powell | 549/255 |
| 4,579,984 | 4/1986 | Neier et al. | 568/897 |
| 4,724,252 | 2/1988 | Rasshofer | 525/452 |
| 4,740,531 | 4/1988 | Rasshofer | 521/167 |

FOREIGN PATENT DOCUMENTS

| | | | |
|---|---|---|---|
| 323138 | 7/1989 | European Pat. Off. | 568/695 |
| 323270 | 7/1989 | European Pat. Off. | 568/897 |

*Primary Examiner*—Howard T. Mars
*Attorney, Agent, or Firm*—Alexander J. McKillop; Charles J. Speciale; Jessica M. Sinnott

[57] ABSTRACT

A process for production of dialkyl ether by hydration and etherification of olefinic feedstock containing at least one lower alkene by contacting the olefinic feedstock and water in a catalytic reaction zone with porous solid metallosilicate acidic catalyst under olefin hydration and etherification conditions. Improvement is achieved by recovering a first fluid effluent stream from the reaction zone; splitting the first fluid effluent stream into a liquid product recovery stream and a fluid recycle stream; and passing the fluid recycle stream consisting essentially of olefin, alcohol and ether in effluent stream proportions for feeding to the reaction zone along with fresh olefinic feedstock and fresh water, wherein the amount of fluid recycle stream is sufficient to maintain a homogeneous single fluid reaction phase in the reaction zone.

9 Claims, 4 Drawing Sheets

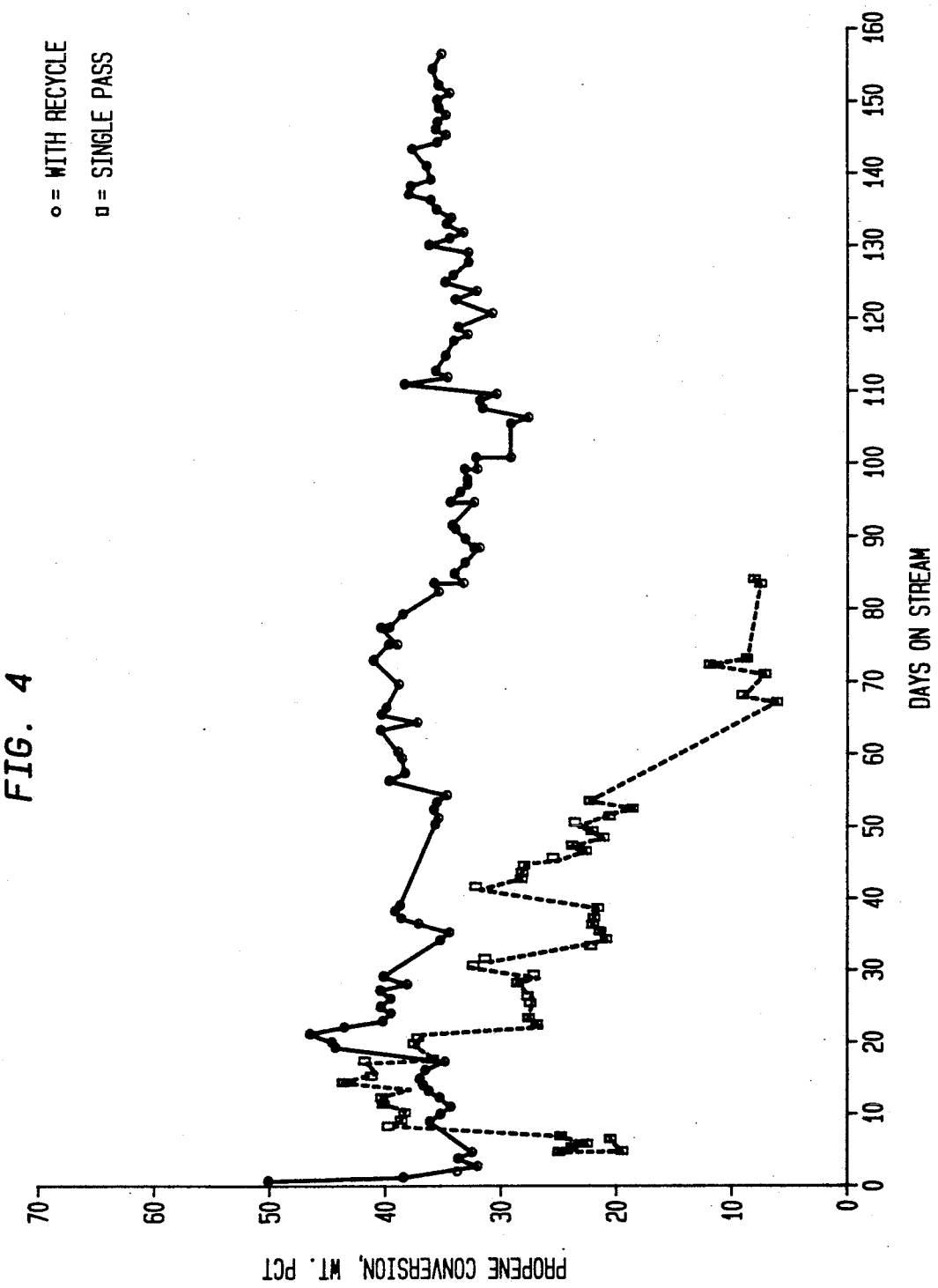

CATALYTIC OLEFIN HYDRATION FOR ETHER PRODUCTION

This invention relates to olefin hydration, especially for production of di-isopropyl ether (DIPE) from $C_{3+}$ olefinic feedstocks. Particularly, the invention relates to a novel technique for operating an adiabatic fixed bed reactor with solid hydration catalyst.

BACKGROUND OF THE INVENTION

The need to eliminate lead-based octane enhancers in gasoline has provided incentive for development of processes to produce high octane gasolines blended with lower aliphatic alkyl ethers as octane boosters. Supplementary fuels are being vigorously developed in the petroleum refining industry. Lower molecular weight alcohols and ethers such as isopropyl alcohol (IPA), isopropyl t-butyl ether (IPTBE), and diisopropyl ether (DIPE) are in the boiling range of gasoline fuels and are known to have a high blending octane number. They are useful octane enhancers. In addition, by-product propene (propylene) from which IPA and DIPE can be made is usually available in a fuels refinery, typically as a $C_{3+}$ aliphatic stream rich in propene and propane. The petrochemicals industry also produces mixtures of light olefin streams in the $C_2$–$C_7$ molecular weight range and the conversion of such streams or fractions thereof to alcohols and/or ethers can also provide products useful as solvents and blending stocks for gasoline.

Adapting available refinery feedstock to produce these oxygenates simultaneously as octane enhancers can involve two different olefin hydration and etherification processes, i.e. propene hydration-etherification to give DIPE and IPA. Accordingly, a challenge is provided to explore these processes to discover how they may be integrated in a manner more beneficial to the production of high octane gasoline.

Catalytic hydration of olefins to provide alcohols and ethers is established technology for production of the IPA and DIPE and is of significant commercial importance. Representative olefin hydration processes are disclosed in U.S. Pat. Nos. 4,334,890 (Kochar); 3,912,463 (Kozlowski et al.); 4,042,633 (Woods); 4,499,313 (Okumura et al.); 4,886,918 (Sorensen et al).

Olefin hydration employing medium pore and large pore zeolite catalyst is a known synthesis method. As disclosed in U.S. Pat. No. 4,214,107 (Chang et al.), lower olefins, in particular propylene, are catalytically hydrated over a crystalline aluminosilicate zeolite catalyst having a silica to alumina ratio of at least 12 and a Constraint Index of from 1 to 12, e.g., acidic ZSM-5 type zeolite, to provide the corresponding alcohol, essentially free of ether and hydrocarbon by-product. Acid resin catalysts such as "Amberlyst 15" may also be used for hydration of light olefins.

Production of ether from secondary alcohols such as isopropanol and light olefins is known. As disclosed in U.S. Pat. No. 4,182,914 (Imaizumi), DIPE is produced from IPA and propylene in a series of operations employing a strongly acidic cation exchange resin as catalyst. Recently, processes for the direct hydration of olefins to provide alcohols and ethers using porous shape selective metallosilicate zeolite catalyst, such as zeolite Beta have been disclosed in U.S. Pat. No. 4,857,664 (Huang et al.), incorporated by reference. Prior processes for hydrating olefins have often been found to be inefficient with regard to catalyst life. Maldistribution of water and hydrocarbon reactants may cause deactivation, especially with solid metallosilicate catalysts having large pores (ie 7+ Angstroms) or medium pores (5–7 A.)

It is a main object of this invention to provide a process for production of oxygenated hydrocarbons by olefin hydration, such as alcohols and/or ethers in a more economical manner and with improved yields of ethers. It is another object of the present invention to provide an improved process for the production of isopropanol and di-isopropyl ether with increased catalyst life.

SUMMARY OF THE INVENTION

An improved process has been discovered for production of alcohol or ether by hydration of olefinic feedstock containing at least one lower alkene by contacting the olefinic feedstock and water in a hydration zone with porous solid metal oxide acidic olefin hydration catalyst under olefin hydration conditions, which comprises: recovering a first liquid effluent stream from at least one fixed bed hydration zone; splitting said first liquid effluent stream into a product recovery stream and a liquid recycle stream; and passing said recycle stream comprising olefin, alcohol and ether in effluent stream proportions for feeding to at least said primary fixed bed hydration zone along with fresh olefinic feedstock and fresh water, wherein the amount of recycle stream is sufficient to maintain a substantially homogeneous single reaction phase in said primary hydration zone. The recycle stream may be combined with fresh feed at a weight ratio of about 5:1 to 10:1 recycle:feed, thereby eliminating water phase separation in the reactants.

The reactor "pump-around" technique provides unexpected increases in product yield and catalyst life, especially in production of DIPE from propylene with porous zeolite catalyst.

These and other advantages and features of the invention will be seen in the description and drawing.

DESCRIPTION OF THE DRAWING

FIG. 4 is a graphic plot of a long term process run simulating the improved process conditions for comparison with conventional processing techniques.

DETAILED DESCRIPTION OF THE INVENTION

The preferred embodiments of the invention are described with reference to propylene hydration and zeolite catalysts. Metric units and parts by weight are employed unless otherwise indicated.

The olefins hydration and etherification process employs the reaction of propylene with water catalyzed by strong acid to form isopropanol. Reaction may be allowed to continue in the hydration zone to form di-isopropyl ether. The operating conditions of the olefin hydration step include a temperature of about 50° to 450° C., preferably from about 130° to about 220° C and most preferably from about 150 to about 200° C. The pressure is about 700 to 24000 kPa (100 to about 3500 psi, preferably about 500-2000 psi). Water to olefin reactant concentrations are maintained at mole ratio of about 0.1 to 30, preferably 0.3-5.

Olefin hydration to provide ethers and alcohols to produce DIPE and byproduct isopropyl alcohol (IPA) is described in U.S. Pat. Nos. 4,214,107; 4,499,313 incorporated herein by reference. The preferred catalytic methods for making DIPE employ porous solid acid catalysts, such as zeolites Y, Beta and/or ZSM-35 aluminosilicate. DIPE etherification conditions may vary widely in choice of temperature, pressure and reaction time. A preferred method reacts propene with water in an adiabatic downflow reactor containing a fixed bed of zeolite Beta at about 90° to 200° C. and pressure of at least 4000 kPa. However, it is understood that the unit operations described herein can be conducted with any number of specific process steps within the skill of the art.

The olefin hydration process of this invention are carried out in liquid phase, supercritical dense phase, or mixtures of these phases in continuous manner using a fixed bed flow reactor. Liquid space velocity, based on total reactor volume is maintained in the range of about 0.1 to about 10/hour when operating continuously.

Various modifications can be made within the inventive concept, especially with regard to reactor system configuration. Although a single reactor bed may be employed, it is advantageous to employ a series of fixed bed reactor units to permit adequate control of reaction conditions, especially temperature and flow parameters.

It may be feasible to recover any unreacted olefin and recycle it to the reactor. Unconverted isopropanol recovered from the final reactor effluent may also be recycled to further conversion to ether.

The preferred hydration/etherification catalyst comprises acidic shape selective porous zeolite having a pore size of about 7-8 Angstroms, such as aluminosilicate zeolite Beta.

Figure 1:
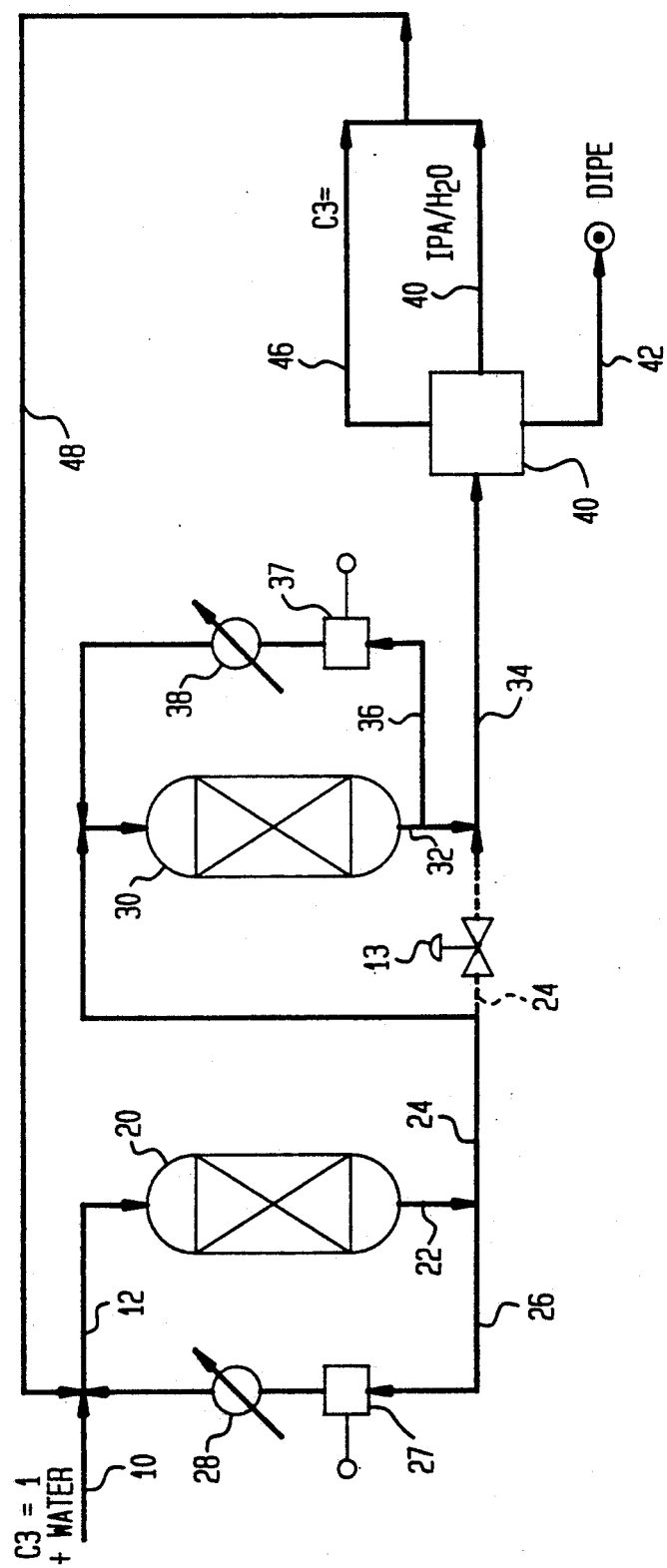
FIG. 1 is a schematic process flow diagram of the improved process.

Referring to FIG. 1 of the drawing, a process flow diagram depicts production of diisopropyl ether by hydration of fresh olefinic feedstock stream 10 containing propene (C3=, propylene) and water reactants, which are passed with recycle streams via line 12 for contacting the propene, water and recycle with porous solid acidic olefin hydration catalyst in a series of reactors. The primary reactor 20 and secondary reactor 30 contain fixed bed adiabatic hydration reaction zones maintained under olefin hydration conditions. Preferrably, at least one hydration reaction zone contains porous zeolite catalyst comprising zeolite Beta. A fluid handling system is operatively connected for recovering a first liquid effluent stream from at least one fixed bed hydration zone. This can be achieved by splitting the first liquid effluent stream 22 into a liquid product recovery stream 24 and a liquid recycle stream 26 having the same composition. The primary reactor 20 is operated continuously by passing the liquid recycle stream 26 substantially unfractionated via flow control means 27 and heat exchanger 28 to feed conduit 12, along with fresh propene feedstock and fresh water. Reaction temperature can be controlled by operation of the cooling rate in recycle stream in unit 28. The amount of unfractionated liquid recycle stream 26 is sufficient to maintain a substantially homogeneous single liquid reaction phase in the primary hydration zone 20 under reaction conditions. The first liquid product stream 24 may be further reacted in second reactor section 30 or, optionally passed via bypass line 24B to the product fractionation system, as described. Unfractionated liquid product recovery stream 24 passed from the primary hydration zone 20 to at least one secondary hydration zone may have a composition the same as the effluent stream 22 and recycle stream 26, consisting essentially of about 10 wt % water, 50 wt% propene, 25 wt% di-isopropyl ether, and 15 wt% isopropanol. It is feasible to remove a portion of the water by cooling the effluent to form a separate aqueous phase for partial recovery of water and isopropanol from reactor effluent prior to recycling the ether/propene-rich non-aqueous phase.

The secondary reactor 30 may be operated with recycle in a manner similar to the primary reactor by splitting second effluent stream 32 to obtain a secondary recycle stream 36, which is passed via flow control means 37 and cooler 38 for combining with first effluent stream 24. Second effluent stream 34, optionally containing a bypass effluent, is fractionated in the product recovery system 40 to recover a di-isopropyl ether stream 42, a byproduct stream 44 containing isopropanol and an unreacted propene stream 46. It is advantgeous to recycle at least stream 44 via line 48 to the primary reactor via line 12, whereby the isopropanol byproduct stream for further conversion to di-isopropyl ether. In the DIPE system depicted, unfractionated liquid recycle stream is passed to the primary hydration zone at a rate of at least about five times the total weight of propene and water reactants in the feedstock (ie-recycle ratio=5:1 to 10:1), thereby eliminating water phase separation in the reactants. It is also possible to operate at higher recycle ratio (ie greater than 10:1) utilizing a single reactor stage (reactor 20) and eliminate second reactor 30 via stream 24B.

In the following examples, 65% zeolite Beta is used in extrudate form with alumina binder; however, other binders such as silica, zirconia, etc may be used. Continuous runs are made, with weight hourly space velocity based on the zeolite content. Unless otherwise indicated, reaction conditions include reactor inlet temperature of about 165° C. and pressure of about 10,000 kPa. Comparative runs for a single zone adiabatic downflow reactor with fixed bed extrudate catalyst. The data in Table 1 show improved net DIPE yields for recycle ratios of 10:1 and 5:1.

TABLE 1

| Mode | Single Pass | Recycle | Single Pass | Recycle |
|---|---|---|---|---|
| Run No. | 1A | 1B | 1C | 1D |
| Days on stream | 6 | 10 | 32 | 39 |
| Fresh Feed Rates | | | | |
| Propene, WHSV | 0.5 | 0.5 | 0.5 | 0.5 |
| Water, WHSV | 0.1 | 0.1 | 0.1 | 0.1 |
| Isopropanol, WHSV* | 0.2 | 0.2 | 0.2 | 0.1 |
| Product Recycle Ratio, wt/wt | 0 | 10 | 0 | 5 |
| Conversions, wt % | | | | |
| Propene | 32.7 | 36.8 | 23.6 | 40.0 |
| Water | 23.5 | 18.7 | 26.5 | 32.0 |
| 2-Propanol | 14.1 | 41.3 | 20.8 | 2.8 |
| DIPE yield wt** | 38.6 | 40.8 | 24.5 | 40.7 |

*Simulates iso-propanol (IPA) recycle
**DIPE yield based on fresh FF Propene, corrected to zero net IPA conversion

TABLE 2

| | Reactor Inlet Composition* | |
|---|---|---|
| Run | (Single Pass) | (Product Recycle)** |
| Propene, wt %/mol % | 62.5/57.3 | 45.1/48.3 |

TABLE 2-continued

| Run | Reactor Inlet Composition* | |
|---|---|---|
| | (Single Pass) | (Product Recycle)** |
| 2-Propanol, wt %/mol % | 25.0/16.0 | 15.6/11.7 |
| Water, wt %/mol % | 12.5/26.7 | 11.0/27.5 |
| DIPE, wt %/mol % | 0 | 24.4/10.8 |
| Oligomer, wt %/mol % | 0 | 3.9/1.7 |
| Total | 100/100 | 100/100 |

*Fresh Feed WHSV (zeolite) of 0.5 $C_3=$ /0.2 IPA/0.1 $H_2O$
**Recycle: Fresh feed weight ratio = 5:1

Reactor feed inlet composition is shown for single pass and "total product recycle" mode operation in Table 2. The process test unit was first streamed in single pass (Run #1), continuous mode, for the first week of operation, after which time recycle was started (Run 1B). The unit was returned briefly to single pass (Run 1C) operation later in other run, causing a significant decline in conversion and yield which was restored when recycle was resumed (Run 1D). Table 1 contains conditions and yields for single pass and recycle operation. Table 2 compares reactor inlet composition with and without recycle.

Figure 2:
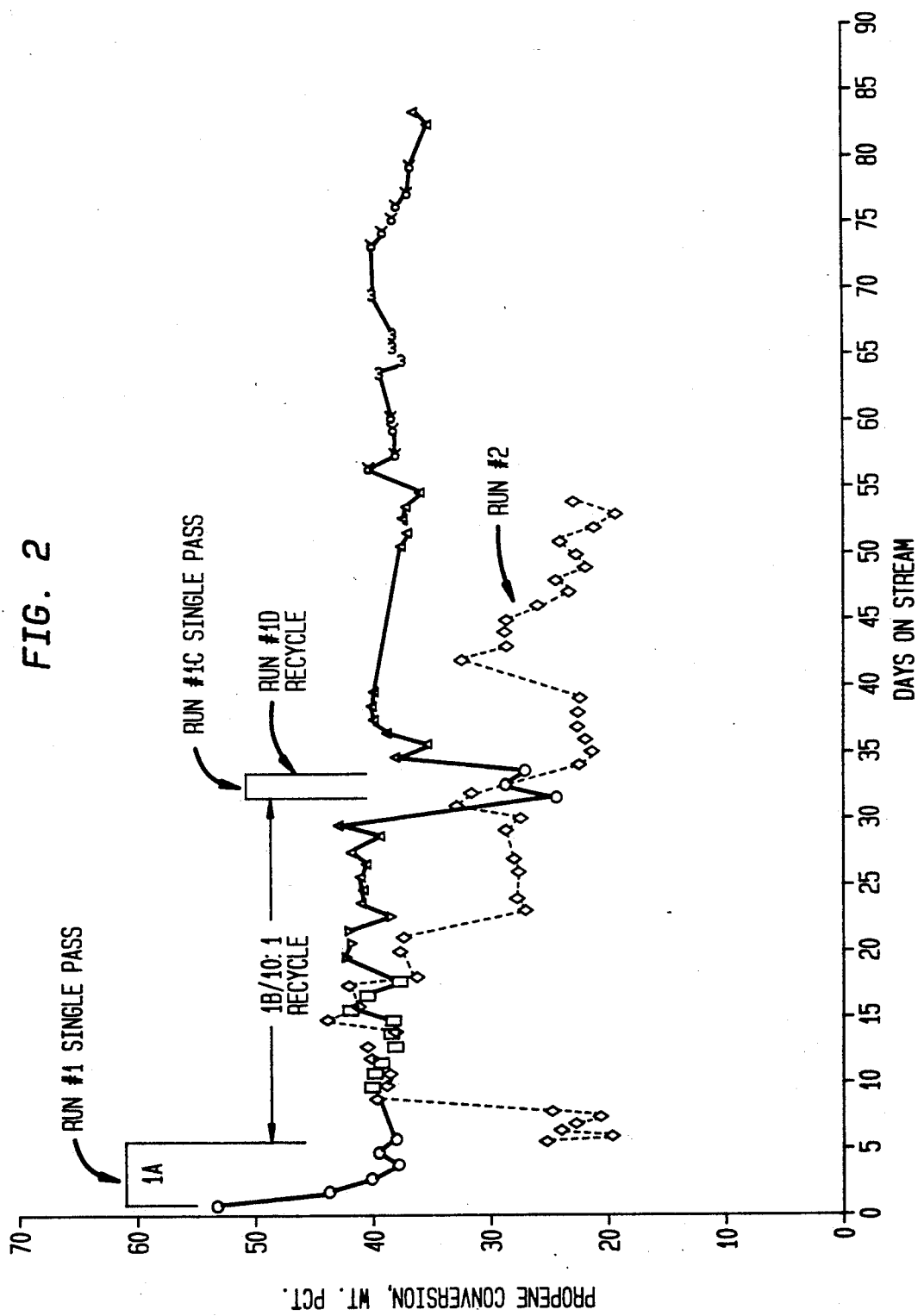
FIG. 2 is a graphic plot of comparative process runs showing improve ether product yields.

A second pilot plant run showed significant aging in single pass operation for 55 days at the same conditions and using the same catalyst. Propene conversion versus days on stream is plotted in FIG. 2 for both runs for comparison purposes.

In fixed bed hydration of propene to di-isopropylether (DIPE), catalyst aging has been found to limit cycle length and catalyst life during single pass operation. When total product recycle is introduced, propene conversion and DIPE yield increase and aging is significantly reduced. This effect is unexpected, since pump-around type of reaction operation generally reduces conversion compared to plug flow (single pass). Catalyst life is increased compared to conventional process flow schemes. Product pumparound recycle is ordinarily expected to lower yields (back-mixed versus plug flow) and reduce catalyst life (coke/polymer formation). The opposite occurs in both instances.

This advantage in yield and catalyst aging is unexpected. Product recycle improves overall distribution in the reactor due to higher flux and improving phase behavior (a single liquid phase versus water-rich and water-lean phases). The increased DIPE at the reactor inlet may act as a solvent to remove coke precursors. The reactor composition, in recycle mode, may improve kinetics (by shifting reaction order).

Figure 3:
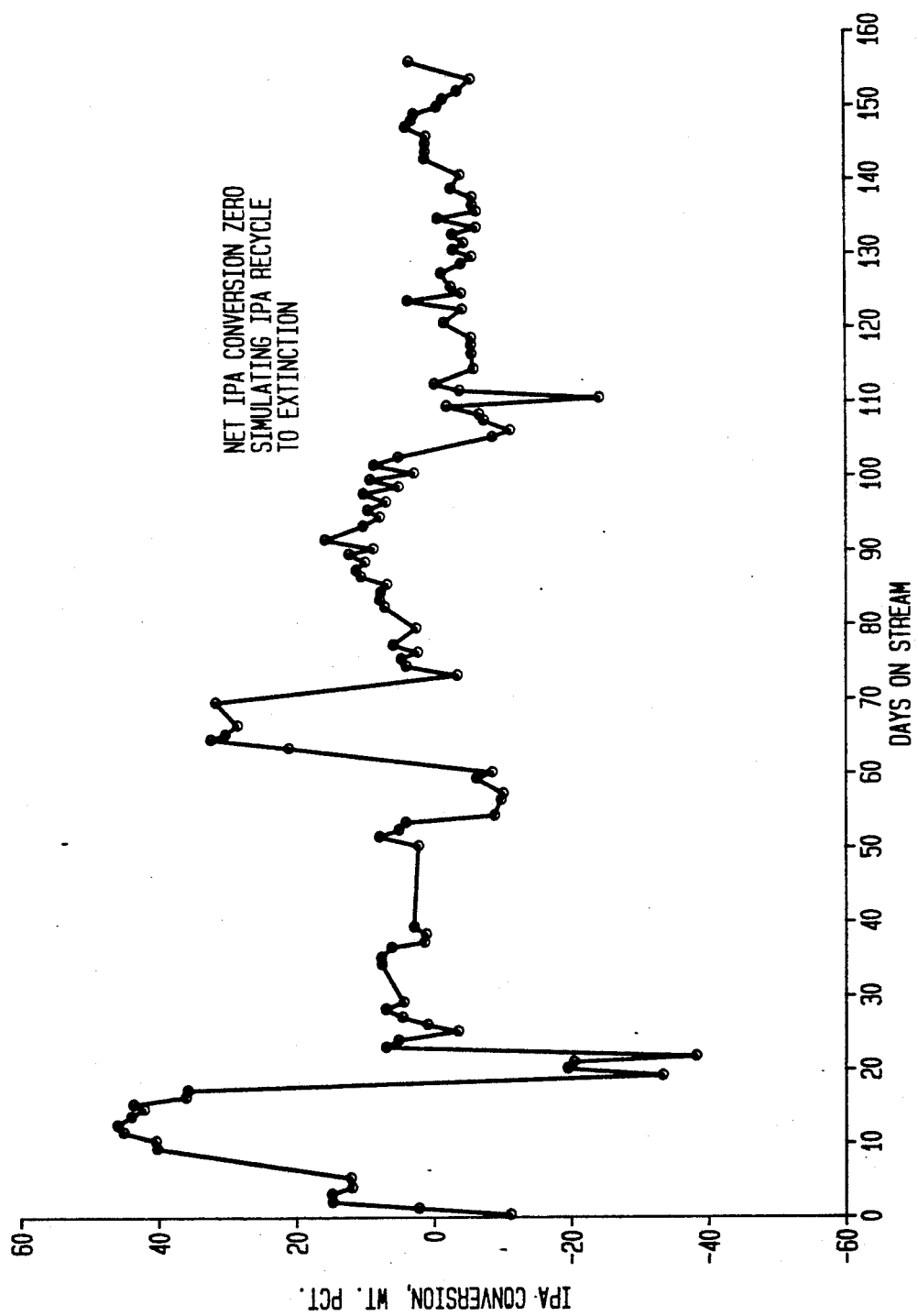
FIG. 3 is a graphic plot of byproduct isopropanol conversion.

Comparative long term pilot plant runs plotted in FIGS. 3 and 4 simulate the recycle pumparound reactor inlet composition, with IPA being used for simulating an IPA recycle loop recycling to extinction. In reactor pumparound mode IPA net conversion was controlled to generally −5 to +5% (see FIG. 3). A comparison of long term process performance with and without pumparound is plotted in FIG. 4. The run using pumparound continued to provide stable performance after 160 days on stream.

It has been found that pumparound improves performance by eliminating multi-liquid phase transport limitations. Only one liquid phase exists in pumparound operation, while at least two exist in single pass operation. This can be observed by viewing a heated sight glass at the reactor inlet (at reactor conditions). This flow scheme provides significant benefits beyond simple heat control. It is possible to adjust pumparound composition by adjusting reactor effluent temperature and recycling a separated ether-rich phase which may provide more improved performance by reducing excess water, which can degrade catalyst integrity.

A theoretical explanation for the observed increase in yields results from the isopropanol/ether saturating the catalyst pores. This prevents the formation of any separate water or olefin phases in the pores during operation. The aqueous or hydrocarbon phases can cause permanent catalyst deactivation. The water phase may attack the crystalline structure of the catalyst, while a highly olefinic phase would deactivate the catalyst via rapid coke formation. The isopropanol/ether mixture also allows controlled quantities of water and propylene to be present homogeneously in the catalyst pores, which allows the reactions to proceed properly at reaction temperature. For the recycle technique to be effective, the recycled liquid must dissolve high concentrations of water and olefin present in fresh feedstock.

While the invention has been described by specific examples and embodiments, there is no intent to limit the inventive concept except as set forth in the following claims.

We claim:

1. A process for the production of diisopropyl ether by hydration and etherification of fresh olefinic feedstock containing propene with water, which comprises the steps of:

contacting the propene feedstock and water with porous solid acidic olefin hydration catalyst in a series of primary and secondary fixed bed reaction zones under olefins hydration and etherification conditions, including at least one reaction zone containing shape selective medium pore zeolite comprising zeolite Beta;

recovering a fluid effluent stream from at least one fixed bed reaction zone;

splitting said fluid effluent stream into a liquid product recovery stream and a fluid recycle stream; and passing said fluid recycle stream substantially unfractionated for feeding to at least said primary fixed bed zone along with fresh propene feedstock and fresh water, wherein the amount of unfractionated fluid recycle stream is sufficient to maintain a single fluid reaction phase in said primary reaction zone.

2. The process of claim 1 wherein the zone reaction conditions comprise temperature of about 165° C. and pressure of about 10,000 kPa.

3. The process of claim 1 wherein said liquid product stream is fractionated to recover a di-isopropyl ether stream, a byproduct stream containing isopropanol and an unreacted propene stream; and wherein said isopropanol byproduct stream is recycled to said primary reaction zone for further conversion to di-isopropyl ether.

4. The process of claim 1 wherein said unfractionated fluid recycle stream is passed to the primary reaction zone at a rate of at least about five times the total weight or propene and water reactants int he feedstock, thereby eliminating water phase separation in the reactants.

5. The process of claim 1 wherein unfractionated liquid product recovery stream is passed from said primary reaction zone to at least one secondary reaction zone in a composition consisting essentially of about 10 wt% water, 50 wt% propene, 25 wt% di-isopropyl ether, and 15 wt% isopropanol.

6. In a process for production of dialkyl ether by hydration and etherification of olefinic feedstock containing at least one lower alkene by contacting the olefinic feedstock and water in a catalytic reaction zone with porous solid metallosilicate acidic catalyst under olefin hydration and etherification conditions, the improvement which comprises:

recovering a fluid effluent stream from the reaction zone;

splitting said fluid effluent stream into a liquid product recovery stream and a fluid recycle stream; and passing said fluid recycle stream consisting essentially of olefin, alcohol and ether to said reaction zone along with fresh olefinic feedstock and fresh water, wherein the amount of fluid recycle stream is sufficient to maintain a homogeneous single fluid reaction phase int he reaction zone.

7. In the process for producing diisopropyl ether by hydration and etherification of feedstock containing propene, which comprises contacting the propene feedstock and water in at least one fixed bed catalystic reaction zone with porous acid zeolite catalyst comprising zeolite Beta under olefins hydration and etherification conditions at reaction temperature of about 50° to 200° C., the improvement which comprises:

recovering a fluid effluent stream from said fixed bed reaction zone;

splitting said fluid effluent stream into a product recovery stream and a fluid recycle stream;

passing said fluid recycle stream without fractionation for feeding to said fixed bed hydration zone for further conversion with propene, wherein the fluid recycle stream is combined with fresh feed in amount sufficient to eliminate water phase separation in the reactants.

8. The process of claim 7 wherein said fixed bed reaction zone is maintained in a vertical downflow reactor having a series of fixed catalyst beds.

9. The process of claim 7 wherein the fluid recycle stream is passed to the reaction zone at a rate of at least about five times the total weight of propene and water reactants in the feedstock, thereby eliminating water phase separation in the reactants; and wherein the fluid recycle stream is passed to the reaction zone in a composition consisting essentially of about 10 wt% water, 50 wt% propene, 25 wt% di-isopropyl ether, and 15 wt% isopropanol.

* * * * *